US008823930B2

(12) United States Patent
Engel

(10) Patent No.: US 8,823,930 B2
(45) Date of Patent: Sep. 2, 2014

(54) APPARATUS AND METHOD FOR INSPECTING AN OBJECT

(71) Applicant: Carl Zeiss Industrielle Messtechnik GmbH, Oberkochen (DE)

(72) Inventor: Thomas Engel, Aalen (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 0 days.

(21) Appl. No.: 13/955,020

(22) Filed: Jul. 31, 2013

(65) Prior Publication Data

US 2014/0043602 A1    Feb. 13, 2014

Related U.S. Application Data

(63) Continuation of application No. PCT/EP2012/065478, filed on Aug. 7, 2012.

(60) Provisional application No. 61/680,495, filed on Aug. 7, 2012.

(51) Int. Cl.
*G01N 21/88* (2006.01)

(52) U.S. Cl.
CPC ..................................... *G01N 21/88* (2013.01)
USPC ..................................... 356/237.5; 356/237.1

(58) Field of Classification Search
CPC ..................................................... G01N 21/88
USPC ............ 356/237.1–237.5; 382/106, 141, 181, 382/282
See application file for complete search history.

(56) References Cited

U.S. PATENT DOCUMENTS

| 6,400,455 | B1 * | 6/2002 | Kurokawa et al. | 356/239.1 |
| 6,496,253 | B1 * | 12/2002 | Vokhmin | 356/124 |
| 6,525,303 | B1 * | 2/2003 | Gladnick | 250/208.1 |
| 6,841,780 | B2 * | 1/2005 | Cofer et al. | 250/341.1 |
| 7,168,822 | B2 * | 1/2007 | Abramovich et al. | 362/249.07 |
| 7,649,628 | B2 | 1/2010 | Wadman | |
| 7,783,104 | B2 * | 8/2010 | Kawaragi | 382/149 |

(Continued)

FOREIGN PATENT DOCUMENTS

| DE | 10 2008 038 256 A1 | 2/2010 |
| DE | 10 2008 041 343 A1 | 2/2010 |

(Continued)

*Primary Examiner* — Sang Nguyen
(74) *Attorney, Agent, or Firm* — Harness, Dickey & Pierce, P.L.C.

(57) ABSTRACT

An apparatus and method for optically inspecting an object, comprising an object carrier for carrying the object, a pattern generating unit for illuminating the object with a measurement pattern, an image capture unit for capturing a number of images of the object, imaging optics for influencing a light beam path between the object and the image capture unit, and a data processing unit for determining at least one property of the object on the basis of the captured images. The apparatus can be set to at least a first operating distance and a second operating distance, and furthermore has a diffusing unit, which can be changed between an active state, in which the diffusing unit influences the light beam path in front of the pattern generating unit and an inactive state, in which the diffusing unit does not influence the light beam path in front of the pattern generating unit.

18 Claims, 6 Drawing Sheets

(56) References Cited

U.S. PATENT DOCUMENTS

| | | | |
|---|---|---|---|
| 2004/0145816 A1* | 7/2004 | Engel | 359/656 |
| 2009/0168039 A1* | 7/2009 | Kok et al. | 355/67 |
| 2010/0177164 A1* | 7/2010 | Zalevsky et al. | 348/46 |
| 2010/0310130 A1* | 12/2010 | Beghuin et al. | 382/106 |
| 2011/0310242 A1 | 12/2011 | Knupfer et al. | |
| 2012/0044504 A1* | 2/2012 | Ohnishi et al. | 356/602 |
| 2012/0086950 A1* | 4/2012 | Sho et al. | 356/601 |

FOREIGN PATENT DOCUMENTS

| | | |
|---|---|---|
| DE | 10 2008 064 562 A1 | 7/2010 |
| DE | 10 2009 021 733 A1 | 12/2010 |
| DE | 10 2010 007 922 A1 | 8/2011 |
| EP | 2 327 956 A1 | 6/2011 |
| EP | 2 442 067 A1 | 4/2012 |
| WO | WO 2009/024756 A1 | 2/2009 |
| WO | WO 2010/020635 A2 | 2/2010 |

* cited by examiner

APPARATUS AND METHOD FOR INSPECTING AN OBJECT

CROSS-REFERENCE TO RELATED APPLICATIONS

This application is a continuation of International PCT application No. PCT/EP2012/065478, filed Aug. 7, 2012. This application also claims the priority of U.S. provisional application No. 61/680,495, filed Aug. 7, 2012. The entire contents of these priority applications are incorporated herein by reference.

BACKGROUND OF THE INVENTION

The present invention relates to an apparatus for optically inspecting an object, comprising an object carrier for carrying the object, a pattern generating unit for illuminating the object with a measurement pattern, an image capture unit for capturing a number of images of the object, an imaging optics for influencing a light beam path between the object and the image capture unit, and a data processing unit, which is designed to determine at least one property of the object on the basis of the number of images.

In accordance with a further aspect, the present invention relates to a method for changing an operating mode of an apparatus for optically inspecting an object.

In the industrial manufacture of products, the product quality has increased in importance for many years. High product quality can be achieved, firstly, by means of appropriately designed and stable manufacturing processes. Secondly, the quality parameters of a product have to be monitored as reliably and fully as possible in order to identify quality deficiencies at an early stage. In many cases, the quality of a product surface is important. This can involve decorative surfaces, such as, for example, paint surfaces in the case of motor vehicles or domestic particles, or technical surfaces, such as, for instance, the surfaces of precision-machined metallic pistons or bearing surfaces.

There are already a large number of proposals and designs for inspecting surfaces.

The document DE 10 2009 021 733 A1 describes for example a deflectormetric method and a corresponding apparatus. This method involves projecting a stripe pattern having a sinusoidal brightness profile onto a screen arranged obliquely above a surface to be inspected. The projected pattern is varied or moved, such that correspondingly varied stripe patterns are incident on the surface. During or after the variation/movement of the pattern, in each case an image of the surface is captured with the reflected pattern. By means of a mathematical combination of the images captured at different points in time, the intention is to generate a result image on the basis of which defective regions and defect-free regions of the surface can be distinguished computationally and/or visually.

Further deflectometry methods are disclosed for example in the documents DE 10 2008 038 256 A1 and DE 10 2008 064 562 A1.

Furthermore, so-called fringe pattern methods or stripe projection methods are known in the prior art. By way of example, the document DE 10 2010 007 922 A1 discloses the use of such a fringe pattern method. In this case, a stripe pattern is projected onto the object to be inspected, for example by an illumination device being directed at the object through a multi-stripe grating. Bright and dark stripes alternate in the multi-stripe grating. The width of the stripes of the multi-stripe grating determines—together with an angle between illumination direction and observation direction—the accuracy or the resolution of the three-dimensional detection of the object. From the position of an illumination device of the multi-stripe grating and the position of the multi-stripe grating, it is possible to calculate the position of a light plane running from the illumination device through the stripes of the multi-stripe grating. On the basis of the position of a pixel in the image of the first image capture device, it is in turn possible to calculate the vector of a light beam that generated said pixel. This in turn makes it possible to determine the point of intersection of said light beam with the calculated plane of the multi-stripe grating. The spatial coordinates of a specific pixel on the image of the image capture unit are thus obtained.

Provision can be made for the stripe projection method to be a Graycode stripe projection method. In principle, bright and dark stripes merely alternate in a multi-stripe pattern. This means, however, that a for example bright pixel in an image of the first image capture device cannot be given an absolute assignment to one of said stripes. Therefore, a so-called Graycode method is used to enable a unique assignment. In this case, by way of example, firstly only one bright and one dark stripe are projected onto the face, in a second step each of said stripes is in turn subdivided into one bright and one dark stripe, such that a total of four stripes are present, in a next step a subdivision is in turn effected, such that eight stripes are present, etc. The subdivision is effected until finally the desired stripe width or resolution is present. If an image of the object is then captured for each stripe resolution, it is possible, on the basis of the bright/dark change, for each pixel to be uniquely assigned a stripe of the stripe grating represented last with the desired resolution.

A further refinement of a fringe pattern method can be a phase shift method, which enables a resolution in a subpixel range. In this case, a sinusoidal brightness profile is modulated on the stripe pattern, which is rectangular per se with regard to its brightness values. A first image capture is then effected, and the phase of the modulated wave is subsequently shifted by $\pi/2$ transversely with respect to the beam direction. This is followed by renewed capture and renewed shifting until a total of at least four images have been captured. From the four brightness values of the pixel in the four captured recordings it is possible to deduce its phase angle within the modulated signal. The exact position of the pixel within a stripe thus becomes determinable.

Further fringe pattern methods are disclosed for instance in the documents DE 10 2008 041 343 A1 and EP 2 327 956 A1.

It is often the case, however, that the known methods and apparatuses can be used only for a specific application, since they presuppose a high level of prior knowledge about the surface to be inspected. Furthermore, alongside a reliable inspection of surfaces, it is also necessary to comply with industrial conditions such as complying with cycle times relevant to incorporation into industrial manufacturing, the capability of carrying out the surface inspection in a factory, and/or the possibility of adapting the surface inspection to changing products simply and rapidly.

What the fringe pattern method and the deflectometry method have in common is that they use stripe patterns having different stripe geometries with regard to stripe width, gap width, duty ratio of stripe and gap, direction or orientation and phase angle.

During use, a fringe pattern method is particularly sensitive to inclinations in a surface of the object and is therefore particularly well suited to identifying topographies. By contrast, a deflectometry method is particularly suitable for identifying depressions and defects in a surface. Deflectometry systems have advantages in use in the case of very smooth, highly reflective to mirroring surfaces. In the case of a surface that is rather rough and reflects incident light less well, that is to say has rather a scattering or absorbing effect, the use of a stripe projection method is generally advantageous.

Against this technical background it is therefore an object of the present invention to specify an apparatus for inspecting an object and a method which eliminate the disadvantages outlined and to enable more variable inspection, in particular of changing objects.

SUMMARY OF THE INVENTION

In accordance with a first aspect of the invention, it is therefore provided an apparatus for optically inspecting an object, comprising an object carrier for carrying the object, a pattern generating unit for illuminating the object with a measurement pattern, an image capture unit for capturing a number of images of the object, an imaging optics for influencing a light beam path between the object and the image capture unit, and a data processing unit, which is designed to determine at least one property of the object on the basis of the number of images, wherein the apparatus can be set to at least a first operating distance and a second operating distance, and the apparatus has a diffusing unit, which can be changed between an active state, in which the diffusing unit influences the light beam path in front of the pattern generating unit and an inactive state, in which the diffusing unit does not influence the light beam path.

It has been recognized that the commonalities of deflectometry method and fringe pattern method can be used to provide an apparatus which makes it possible to inspect an object both in the case of rough, rather scattering surfaces and in the case of smooth, rather mirroring surfaces. In the case of a stripe projection method, however, the measurement pattern is projected onto the object. In the case of a deflectometry method, by contrast, the measurement pattern is observed directly at the location of its originating via the object. In the case of a deflectometry method, therefore, the object is part of the light beam path that emerges from the pattern generating unit and is imaged onto the image capture unit.

The "measurement pattern" can be a stripe pattern or a one-dimensional pattern. However, the measurement pattern can also be a two-dimensional pattern. Both the one-dimensional pattern and the two-dimensional pattern can be spatially coded or uncoded. Examples thereof can be found for instance in the document EP 2442 067 A1.

As pattern generating unit, by way of example, a digital projector or a pattern generator using known Beamer technology is suitable both in a deflectometry method and in a fringe pattern method. Slide projectors can also be used. Furthermore, structured light sources having LEDs (light emitting diodes), OLEDs (organic light emitting diodes) and/or LASER (light amplification through stimulated emission of radiation) are also appropriate. The pattern generating unit generates a measurement pattern which can be set in a variable manner.

In the context of the present application, "operating distance" can be understood to mean an optical operating distance or a mechanical operating distance. The "mechanical operating distance" is the clear distance between a first, object-side disturbing contour of the lens and the measurement object. The "optical operating distance" is the clear distance between a first, object-side disturbing contour of the lens and a focal plane of the lens. In other words, the optical operating distance is the object-side vertex focal length of the imaging optics. The first, object-side disturbing contour can be, for example, a front lens element, i.e. the lens element arranged furthest on the object side, of the imaging optics, its mount or a cover glass of the imaging optics.

In the case of the proposed apparatus, the mechanical operating distance and/or the optical operating distance can be settable. The apparatus can thus be settable at least either to a first mechanical operating distance and a second mechanical operating distance or to a first optical operating distance and a second optical operating distance. In particular, the apparatus can also be settable both to a first mechanical operating distance and a second mechanical operating distance and to a first optical operating distance and a second optical operating distance.

The mechanical operating distance can be settable by, for example, the imaging optics and the object carrier being movable relative to one another. In this way, the mechanical operating distance can be set for example by mechanical movement of the imaging optics.

The optical operating distance can be settable by a focal length of the imaging optics being settable. In this way, the imaging optics is able to operate with a relatively short operating distance in a fringe pattern method and with a relatively long operating distance in a deflectometry method. Since the image capture resolution decreases at relatively long operating distances, such a sequence also appropriately matches the respective applications. In the case of stripe projection, the measurement of a topography is generally of primary importance. In the context of a deflectometry method, however, a purely qualitative check for surface damage is generally of primary importance, which requires a lower accuracy.

In the proposed apparatus, the optical operating distance and the mechanical operating distance can be settable alternatively or cumulatively. If both the optical operating distance and the mechanical operating distance of the apparatus are settable, it is therefore also possible for the operating distance of the apparatus to be set partly by variation of the mechanical operating distance and partly by variation of the optical operating distance—that is to say by a mixed form.

In particular, the apparatus can be set to a first operating mode, in which the optical operating distance corresponds to the mechanical operating distance, and to a second operating mode, in which the optical operating distance is greater than the mechanical operating distance. A fringe pattern method can then be carried out in the first operating mode and a deflectometry method can then be carried out in the second operating mode.

The measurement pattern is projected onto the object from the pattern generating unit in the fringe pattern method. In the deflectometry method, the measurement pattern is diffused by the diffusing plate element and imaged via the object and the imaging optics onto the image capture unit. Consequently, the diffusing unit is not required in the fringe pattern method, whereas it is necessary in the deflectometry method. An "active state" is thus understood to mean that the diffusing unit influences a light beam path of the light emitted by the pattern generating unit. An "inactive state" is understood to mean that the diffusing unit does not influence the light beam path of the light emitted by the pattern generating unit. An active state can be achieved, for example, by the diffusing unit being moved, such that it is no longer situated in the light beam path. However, it can also be provided that the diffusing unit is electrically drivable and is switchable optionally to be active or inactive.

The "diffusing unit" can be embodied as a diffusing plate unit. However, it can also be embodied as a volume diffusing unit. Diffusion can take place at one or both surfaces of the diffusing unit or else in a diffusing volume.

The proposed combined apparatus which is variable in terms of its operating distance is able, in a manner adapted to the properties of the object, such as, for example, the surface quality, degree of luster or absorption behavior, to be used either for the measurement task of topography/3d geometry with the fringe pattern method or for the measurement task of quality/visual inspection with the deflectometry method.

In the context of the present invention, "light" is understood to mean any electromagnetic wave. This holds true, in particular, independently of whether it lies in a spectral range visible to the human eye or, for instance, in an ultraviolet or infrared spectral range. The bandwidth of the radiation used can be chosen as desired. All types of illumination are conceivable from monochromatic light to wide-band white light.

The apparatus is suitable in particular for use in coordinate measuring machines. However, it can also find application in all other measuring systems such as multi-sensor measuring systems, for instance, or alternatively in material microscopes or manufacturing machines.

In accordance with a second aspect of the invention, therefore, a method for changing an operating mode of an apparatus for optically inspecting an object is provided, wherein the apparatus comprises an object carrier for carrying the object, a pattern generating unit for illuminating the object with a measurement pattern, an image capture unit for capturing a number of images of the object, an imaging optics for influencing a light beam path between the object and the image capture unit, wherein the apparatus can be set at least to a first operating distance and to a second operating distance, a data processing unit, which is designed to determine at least one property of the object on the basis of the number of images and to control the apparatus, and a diffusing unit, which can be changed between an active state, in which the diffusing unit influences a light beam path in front of the pattern generating unit and an inactive state, in which the diffusing unit does not influence the light beam path, in front of the pattern generating unit, comprising the following steps:

assigning the first operating distance and the inactive state to a first operating mode, assigning the second operating distance, which is greater than the first operating distance, and the active state to a second operating mode, changing between the first operating mode and the second operating mode by changing the operating distance of the imaging optics between the first operating distance and the second operating distance and changing the diffusing unit from the active state to the inactive state.

In accordance with one refinement of the apparatus according to the first aspect it is proposed that the diffusing unit, for the purpose of changing between the active state and the inactive state, is optionally movable into a light beam path in front of the pattern generating unit by the data processing unit by means of an actuator.

As a result, the change between the active state and the inactive state can be provided structurally relatively simply in a mechanical manner, i.e. by movement of the diffusing unit.

In accordance with a further refinement of the apparatus according to the first aspect it is proposed that the diffusing unit is an etched substrate or a diffractive optical element or a holographic optical element.

In this way, the diffusing unit can be provided in a manner that is advantageous for the respective application. Examples of etched diffusing plates can be found for instance in the document DE 102 20 045 A1.

In accordance with a further refinement of the apparatus according to the first aspect it is proposed that the diffusing unit is an electrically drivable diffusing unit which is switchable between at least one diffusing setting and one non-diffusing setting by the data processing unit.

As a result, the switching of the diffusing unit between the active state and the inactive state becomes possible in a rapid manner. Moreover, a movement of the diffusing unit can be avoided. Examples are LCD screens in which the liquid crystals optionally can be activated in a diffusing manner or have only a transmissive effect in an inactive state. By way of example, reference is also made to the document DE 10 2009 025 362 A1.

In accordance with a further refinement of the apparatus according to the first aspect it is proposed that the pattern generating unit has a pattern generator for generating a measurement pattern and an imaging device for imaging the measurement pattern onto the object.

It can thereby be ensured that the measurement pattern is imaged sharply onto the object by means of the imaging device.

In accordance with a further refinement of the apparatus according to the first aspect it is proposed that the imaging optics is a lens or an objective that is telecentric at the first optical operating distance on the object side or on both sides.

A lens or an objective which is telecentric on both sides is distinguished, in particular, by the fact that theoretically no geometrical image aberrations occur. By way of example, an objective which is telecentric on both sides has no distortion. Moreover, it is possible to change the focusing without varying the imaging scale.

In accordance with a further refinement of the apparatus according to the first aspect it is proposed that the imaging optics is furthermore a zoom objective or a zoom lens.

For the variable selection of the system magnification appropriately for the requirements of the measurement features, it is possible to provide a zoom range of at least 10-fold, maximally up to approximately 20-fold; the zoom range should preferably be approximately 12-fold. Even if only a zoom of approximately 12-fold is required in use, it is possible to operate for measuring machines with other measurement ranges and dimensions through multiple use of the components with a high degree of identical parts in manufacturing. With a restriction of the zoom range, typically the structural length of the system is shortened and structural size and weight are thus saved. This property is particularly important if the construction of small compact systems is involved. In this way, by way of example, it is also possible to provide a compact system that can also be used in the case of rotary-pivoting joints. The design can be implemented for a magnification range of 0.5× to 6×, a 12-fold zoom range.

In accordance with a further refinement of the apparatus according to the first aspect it is proposed that the imaging optics can be set to a first optical operating distance, a second optical operating distance and a third optical operating distance.

Particularly for telecentric operation, the optical system is intended to have a specific standard operating distance. However, since industrial metrology also involves examining objects that are not only planar, it may be necessary also to enable other operating distances. For example for observations of deep bores or within relatively large three-dimensional bodies it can happen that the standard operating distance does not suffice for focusing onto the desired observation plane. Different operating distances are also required for the deflectometry method and the fringe pattern method.

Therefore, it is proposed also to support one or more larger or smaller optical operating distances with the imaging optics. Since the optical unit cannot be optimally designed for a plurality of operating distances simultaneously, reduced expectations in terms of the imaging quality are also accepted in the case of an enlarged operating distance. On account of the enlargement of the operating distance, a reduced numerical aperture and thus a poorer optical resolution in the image inevitably occur. Effects of distortion and chromatic aberrations can also be accepted within certain limits in the case of an enlarged or reduced operating distance.

On the other hand, it is the case that a kind of macro function can be very helpful for a higher resolution. In this case, it is expedient to have a setting of the imaging optics which has a significantly reduced operating distance for high imaging quality. Since very high resolution is involved here, this operating mode should also expediently be combined only with high magnifications. If appropriate, it is expedient also to keep available a higher magnification in the macro mode than that available at the standard operating distance.

In accordance with a further refinement of the apparatus according to the first aspect it is proposed that the data processing unit is designed to control the state of the diffusing unit and the operating distance of the apparatus. In particular, it can furthermore be provided that the data processing unit is furthermore designed to control a magnification or an imaging scale of the imaging optics.

In particular, in this case, in accordance with a further refinement of the apparatus according to the first aspect it can be provided that the apparatus is designed in such a way that, in a first operating mode, the first operating distance is set and the inactive state is chosen, and that, in a second operating mode, the second operating distance, which is, in particular, greater than the first operating distance, and the active state are chosen.

In this way, it becomes possible for the measuring method that is to be applied to be able to be set automatically by means of the data processing unit. All components can be set by the data processing unit on the basis of the measuring method chosen.

In accordance with a further refinement of the apparatus according to the first aspect it is proposed that the second optical operating distance is two to two-and-a-half times the magnitude of the first optical operating distance.

In particular, in accordance with a further refinement of the apparatus according to the first aspect it is proposed that the first optical operating distance is 80 mm and the second optical operating distance is 200 mm, or that the first optical operating distance is 40 mm and the second optical operating distance is 80 mm.

With practical magnitudes that have proved worthwhile in practice, it is thus possible to comply with the requirements made of a standard operating distance of 80 mm, an enlarged operating distance of 200 mm and an above-explained macro operating distance of 40 mm. In this case, an imaging that is telecentric on both sides can be effected at the standard operating distance. An imaging with reduced optical imaging quality in conjunction with adapted magnification and with a restricted numerical aperture can be effected at the enlarged operating distance. The macro operating distance is expedient for high magnifications and images telecentrically as far as possible on both sides.

In accordance with a further refinement of the apparatus according to the first aspect it is proposed that the data processing unit is designed to carry out as first operating mode a fringe pattern method and as second operating mode a deflectometry method for optically inspecting the object.

Likewise, in accordance with one refinement of the method according to the second aspect it is proposed that the first operating mode is a fringe pattern method and the second operating mode is a deflectometry method.

In particular, therefore, at an operating distance of 80 mm it is possible to carry out the stripe projection method, and at an operating distance of 200 mm it is possible to carry out the deflectometry method. Alternatively, however, at an operating distance of 40 mm it is also possible to carry out the stripe projection method, and at an operating distance of 200 mm it is also possible to carry out the deflectometry method. In a further alternative, at an operating distance of 40 mm it is possible to carry out the stripe projection method, and at an operating distance of 80 mm it is possible to carry out the deflectometry method.

It goes without saying that the features mentioned above and those yet to be explained below can be used not only in the combination respectively indicated, but also in other combinations or by themselves, without departing from the scope of the present invention.

BRIEF DESCRIPTION OF THE DRAWINGS

Exemplary embodiments of the invention are illustrated in the drawing and are explained in greater detail in the following description. In the figures.

DETAILED DESCRIPTION OF THE INVENTION

Figure 1:
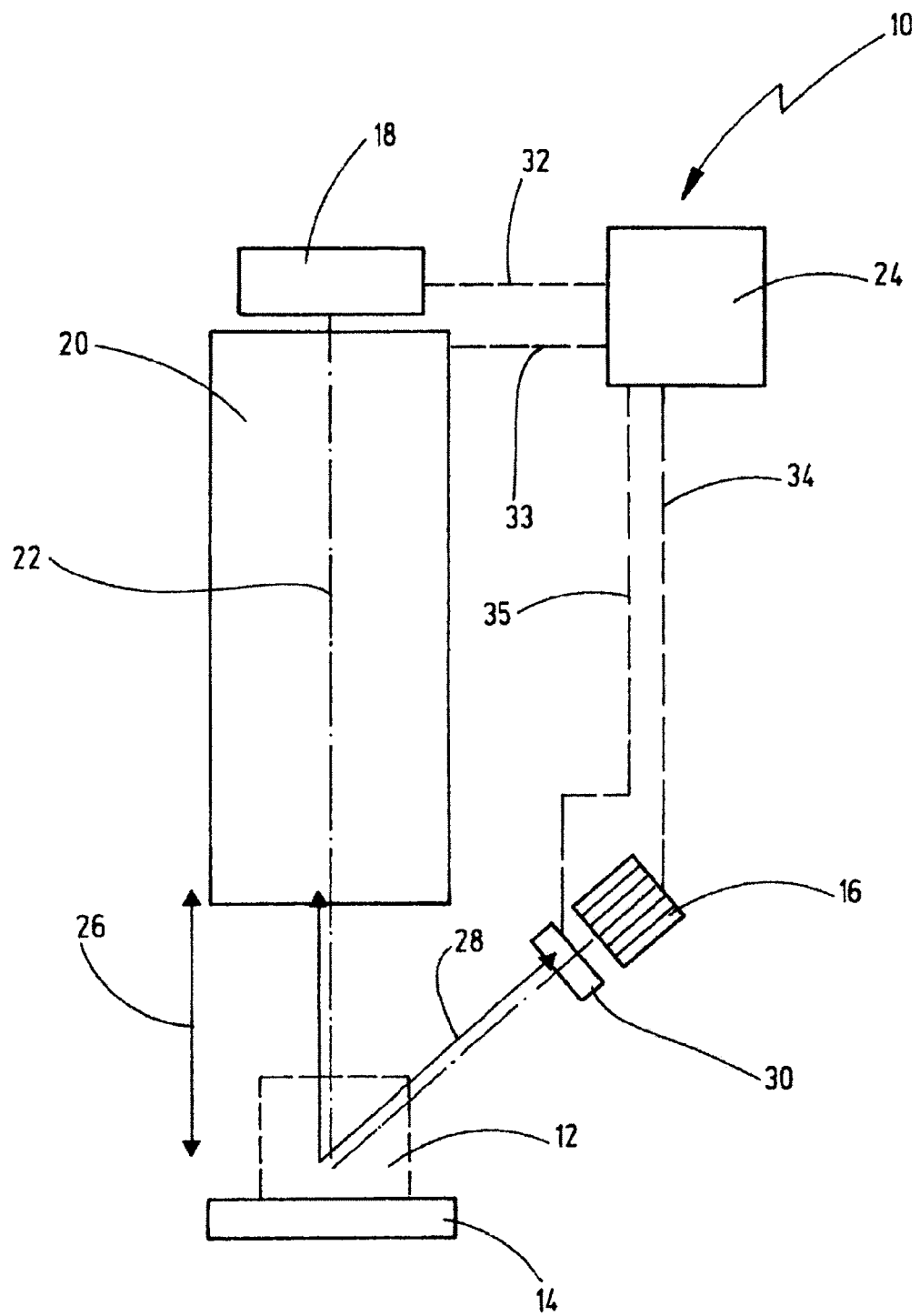
FIG. 1 shows a schematic view of an exemplary embodiment of an apparatus in accordance with the present invention.

FIG. 1 shows an apparatus 10 for inspecting an object 12. The object 12 is arranged on an object carrier 14. By way of example, the object carrier 14 can be an X-Y table, a rotary table or alternatively just a baseplate.

Firstly, the stripe projection method has become established for the simple measurement of a topography of an object 12 within a field of view of a camera. In this case, a measurement pattern is projected onto the object 12 and this image object with the illuminated stripes is captured by a camera. If a plurality of images is then captured with different measurement patterns, the topography of the object 12 can be deduced from the image sequence together with knowledge of the measurement pattern used. Such a method functions particularly in the case of matt or slightly diffusing objects. In the case of lustrous objects it increasingly happens that a large portion of the intensity of the illumination is deflected by reflection on the lustrous object 12 such that it is no longer detected and imaged by the camera. The object is therefore illuminated with a measurement pattern in the stripe projection method. Consequently, it is necessary to provide an interface to an illumination to which a stripe projector that is as compact as possible can be connected. The stripe projection has to be supplied with the electrical power for driving the light source, for example an LED, or for the operation of a pattern generator. For driving the pattern generator, a corresponding line for driving must also be available. Furthermore, it is advantageous if the operation of the pattern generator is also synchronized with the temporal sequence of the camera for image capture, in order that a pattern is respectively available during an image capture. Moreover, the illumination pattern has to be modified between the different image captures.

Secondly the deflectometry method can be employed for inspecting the object 12. In the case of a deflectometry method, the stripes of the measurement pattern are no longer imaged or projected onto the object 12, rather a camera captures the measurement pattern on an illumination screen via a lustrous and reflective surface of the object 12. As a result, the surface of the object 12 becomes part of the optical path or of the light beam path. Here, too, a superimposition of a measurement pattern and the surface of the object arises during imaging. If the measurement patterns are varied between the image captures here, too, then the topography of the object 12 can also be deduced in a manner corresponding to that in the case of stripe projection. In particular, purely qualitative unevennesses and/or damage of a surface of the object 12 can also be perceived.

The difference between the methods therefore consists in the fact that in the case of a stripe projection method the measurement pattern is projected onto the object 12, while in the case of a deflectometry method the measurement pattern is viewed and captured from a corresponding screen by the camera by way of the object. By means of the apparatus 10 explained below, the changeover from a stripe projection method to a deflectometry method can be effected in a simple manner by, for example, a matt plate, generally a diffusing unit, optionally being inserted into the light beam path, in particular in front of the stripe projector.

In order therefore to provide the apparatus 10 with such flexibility with regard to the measuring method to be applied, the apparatus 10 has a pattern generating unit 16. The pattern generating unit 16 is provided for generating and imitating a measurement pattern. In this case, the measurement pattern can be varied over time. In this case, the variation can concern for example the number or the width of the stripes and gaps between the stripes. The stripes can also be provided with a sinusoidal or rectangular intensity profile.

Furthermore, the apparatus 10 has an image capture unit 18. The image capture unit 18 can be a camera or a video camera, for example, which is able, for example in a manner temporally coupled to the generation of the patterns in the pattern generating unit 16, to capture and store images of the object 12. Furthermore, an imaging optics 20 is provided. The imaging optics 20 serves for imaging the object 12 onto the image capture unit 18 in a suitable manner. In particular, the imaging optics 20 is a lens which is telecentric on both sides.

A light beam path is designated by the reference sign 22. In the context of the present application, "light" is understood to mean any electromagnetic wave, in particular including light in a wavelength range not visible to the human eye, for example infrared radiation. The light emitted by the pattern generating unit 16 is therefore incident on the object 12 and then further on the image capture unit 18 through the imaging optics 20.

Furthermore, a data processing unit 24 is provided. The data processing unit 24 serves to control all elements of the apparatus 10 and—depending on the measuring method chosen—to evaluate the images made by the image capture unit 18 with regard to the desired properties of the object 12. In particular, the data processing unit 24 has the task of performing the settings and sequences within the apparatus 10 and also of correspondingly coordinating them in an expedient succession. The main tasks of the data processing unit 24 can be the setting of all the required components in the apparatus 10, the coordination of the sequences in the apparatus 10 in a technically expedient order, the setting of a zoom system of the imaging optics 20 to a desired position, and in this case also the management of the different sequences of the zoom process for the different functions, for example magnification, operating distance, chromatic imaging setting, etc. Furthermore, a setting of an illumination system of the apparatus 10 and also an automatic optimization of the illumination settings for different objects and/or measuring methods can be the task of the data processing unit 24. The data processing unit 24 can be designed for controlling all the required operating parameters of the image capture unit 18, such as, for instance, exposure time, amplification and gamma correction, if appropriate depending on the light wavelength chosen. Furthermore, the data processing unit 24 can coordinate the communication with a further control unit, for example for positioning a carrier system and/or travel movements during a measuring process.

In FIG. 1, the data processing unit 24 is schematically illustrated merely as one block. However, it is entirely possible for this also to involve a plurality of data processing units which, in particular, are also spatially separated from one another and which communicate with one another.

The apparatus 10 has at least a first operating distance 26 and a second operating distance 28. In this case, "operating distance" can be understood to mean a mechanical and/or an optical operating distance. The optical operating distance of the apparatus 10 is preferably settable. At the first operating distance 26, therefore, the focal plane or object-side focal length is at the level of the object 12. That is to say that the imaging optics 20 is focused onto the object 12 or the imaging optics 20 is positioned relative to the object 12 in such a way that the focal plane of the imaging optics 20 lies on the object 12. The stripes projected onto the object 12 are then viewed in the context of the fringe pattern method.

Furthermore, the apparatus 10 has a diffusing unit 30, which diffuses the measurement patterns generated by the pattern generating unit 16. Said measurement patterns are then reflected from the object 12 and imaged onto the image capture unit 18 by the imaging optics 20. The image capture unit 18 then views the measurement pattern on the diffusing unit 30 via the imaging optics 20 and the object 12. A deflectometry method is then carried out. In this case, the focal plane of the imaging optics 20 is then set to the second operating distance 28 or the imaging optics 20 is positioned relative to the object 12 in such a way that the focal plane of the imaging optics 20 lies on the diffusing unit 30. Consequently, the second optical operating distance 28 is greater than the first optical operating distance 26.

If a deflectometry method is carried out, the optical operating distance of the apparatus is therefore greater than the mechanical operating distance of the apparatus. If a fringe pattern method is carried out, the optical operating distance of the apparatus corresponds to the mechanical operating distance of the apparatus. Therefore, the mechanical and/or the optical operating distance can be set in the proposed apparatus. In this way, the ratio between optical operating distance and mechanical operating distance can be set appropriately for the measurement method to be carried out in each case.

By way of example, the first operating distance 26 can be 80 mm and the second operating distance 28 can be 200 mm. A communication of the data processing unit 24 with the image capture unit 18, the imaging optics 20, the pattern generating unit 16 and/or the diffusing unit 30 can be effected in both wired and wireless fashion. The wired communication can be provided by means of electrical and/or optical data transmission, for example.

The diffusing unit 30 is preferably arranged in the light beam path 22 between the object 12 and the pattern generating unit 16. This means that the diffusing unit 30 is arranged in front of the pattern generating unit 16. The diffusing unit 30 can be either in an active state, in which it influences the light beam path 22, but it can also be in an inactive state, in which it does not influence the light beam path 22.

In this case, it is possible for the diffusing unit 30 to be situated in the light beam path 22 at any time. In this case, the diffusing unit 30 can be electrically drivable for example in such a way that its refractive properties can be changed in an electrically driven manner. However, it goes without saying that it can also be provided that the diffusing unit 30 can be moved mechanically, for example by means of an actuator, such that it is optionally movable into and out of the light beam path 22. In this case, the diffusing unit 30 can be, for example, an element produced by etching, a diffractive optical element or a holographic optical element.

The lines 32, 33, 34 and 35 illustrated for the communication of the data processing unit 24 with the imaging optics 20, the image capture unit 18, the pattern generating unit 16 and the diffusing unit 30 are illustrated merely for clarifying the communication and control paths. As already explained above, optionally a wireless, but also a wired, communication connection can be involved in each case.

Figure 2:
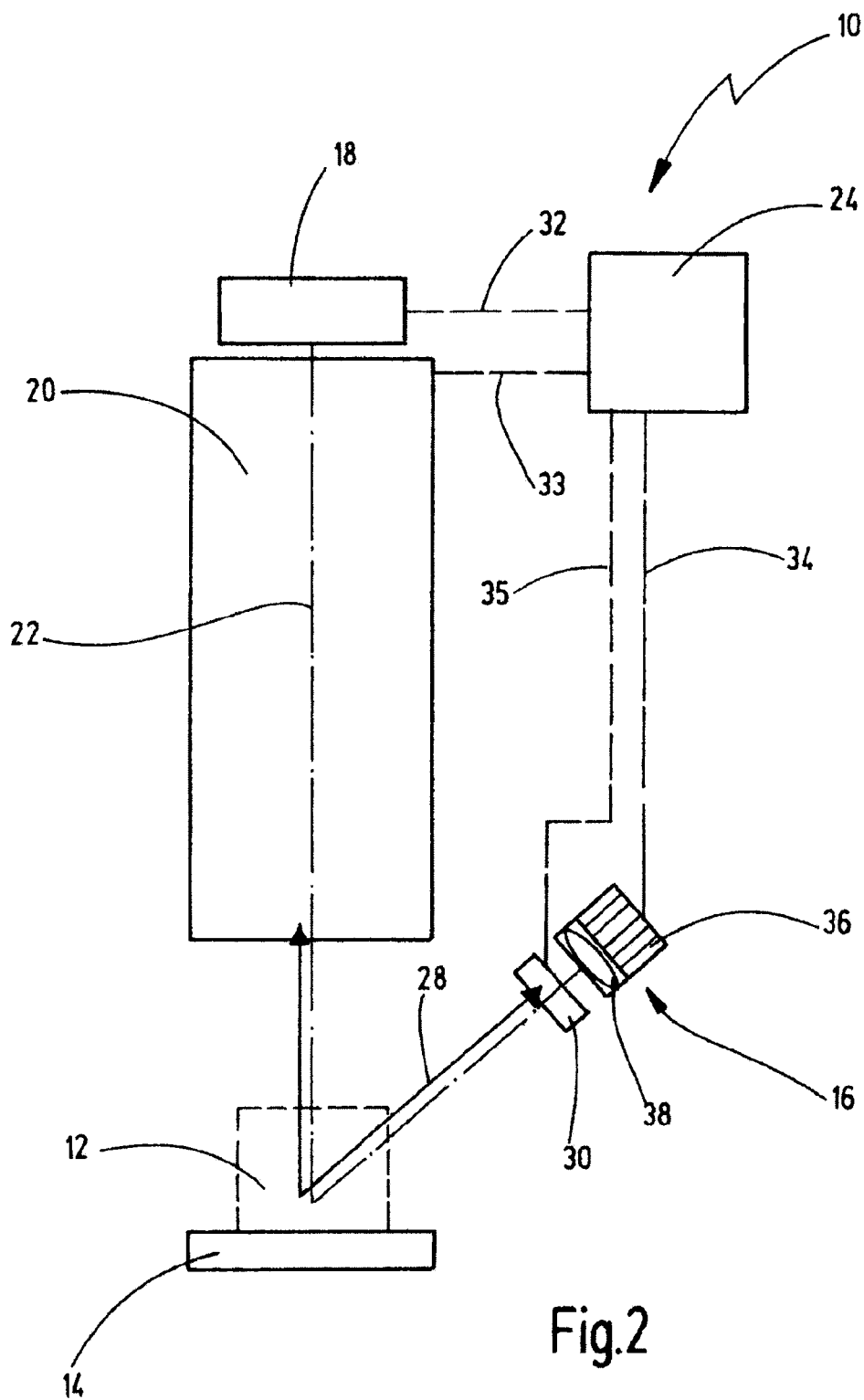
FIG. 2 shows a schematic view of the apparatus in FIG. 1 in an operating mode for carrying out a deflectometry method.

FIG. 2 shows the apparatus 10 from FIG. 1 in a setting for carrying out a deflectometry method.

The pattern generating unit 16 is illustrated in detail. The pattern generating unit 16 can have, in particular, a pattern generator 36 for generating the measurement pattern. Furthermore, an imaging device 38 can be provided, which is designed to image the measurement patterns onto the object 12 in a suitable manner, if this is necessary.

In the deflectometry method, the diffusing unit 30 is in an active state. As illustrated, it can for example be situated in the light beam path 22 and diffuse the measurement pattern generated by the pattern generating unit 16. The image capture unit 18 then looks as it were via the object 12 at the diffusing unit 30 and the measurement pattern emerging therefrom. The imaging optics 20 is set to the second operating distance 28.

Figure 3:
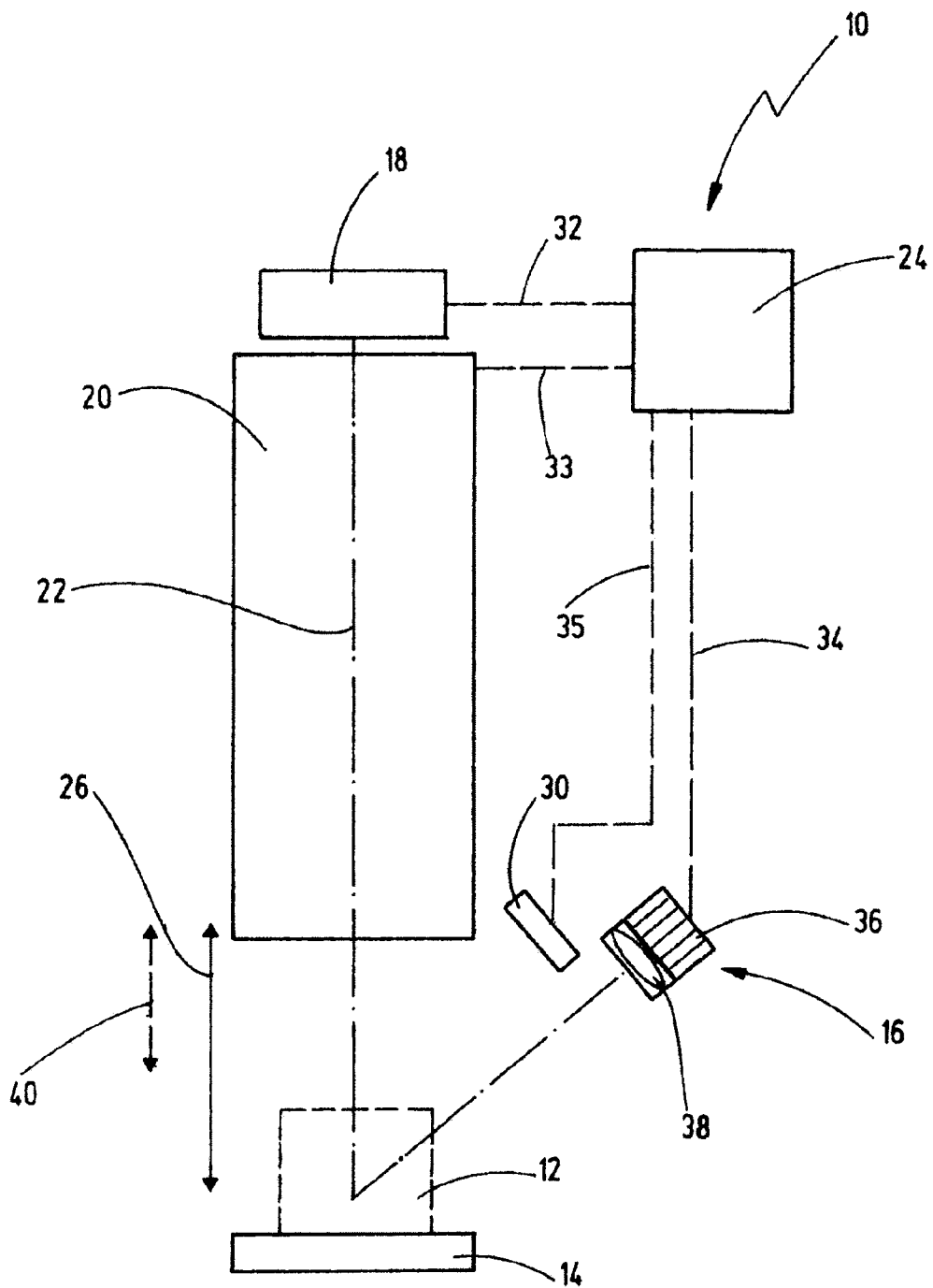
FIG. 3 shows a schematic view of the apparatus in FIG. 1 in an operating mode for carrying out a fringe pattern method.

FIG. 3, by contrast, illustrates the setting of the apparatus 10 for carrying out the stripe projection method. As can be discerned, the diffusing unit 30 is now in an inactive state. By way of example, it may no longer be situated spatially in the light beam path 22. Alternatively, as has already been explained above, an electronic driving of the diffusing unit 30 can also be provided.

The imaging optics 20 is now set to a first operating distance 26, which is less than the second operating distance 28. The object 12 is now viewed, together with the measurement pattern projected onto the object 12.

Furthermore, FIG. 3 schematically indicates a third operating distance 40, which can be less than the first operating distance 26. In principle, it is also possible to use the third operating distance 40 for the stripe projection method and then for example the first operating distance 26—of course via the object 12 to the diffusing unit 30—for implementation for a deflectometry method. As a last alternative it is also conceivable, of course, to use the second operating distance 28 together with the third operating distance 40. The first operating distance 26 can be 80 mm, for example, the second operating distance 28 can be 200 mm, for example, and the third operating distance 40 can be 40 mm, for example.

The spatial arrangement of the imaging optics 20 relative to the pattern generating unit 16 or the object 12 should be understood to be merely by way of example. Preferably, an angle of approximately 45° should be present for example between the optical axes of the imaging optics 20 and the imaging device 38. That is to say that the light beam path 22 has approximately a bend of 45° at an object 12. In principle, however, other angles or instances of coupling in beams are also conceivable, of course, such that other geometrical arrangements can arise therefrom.

Figure 4:
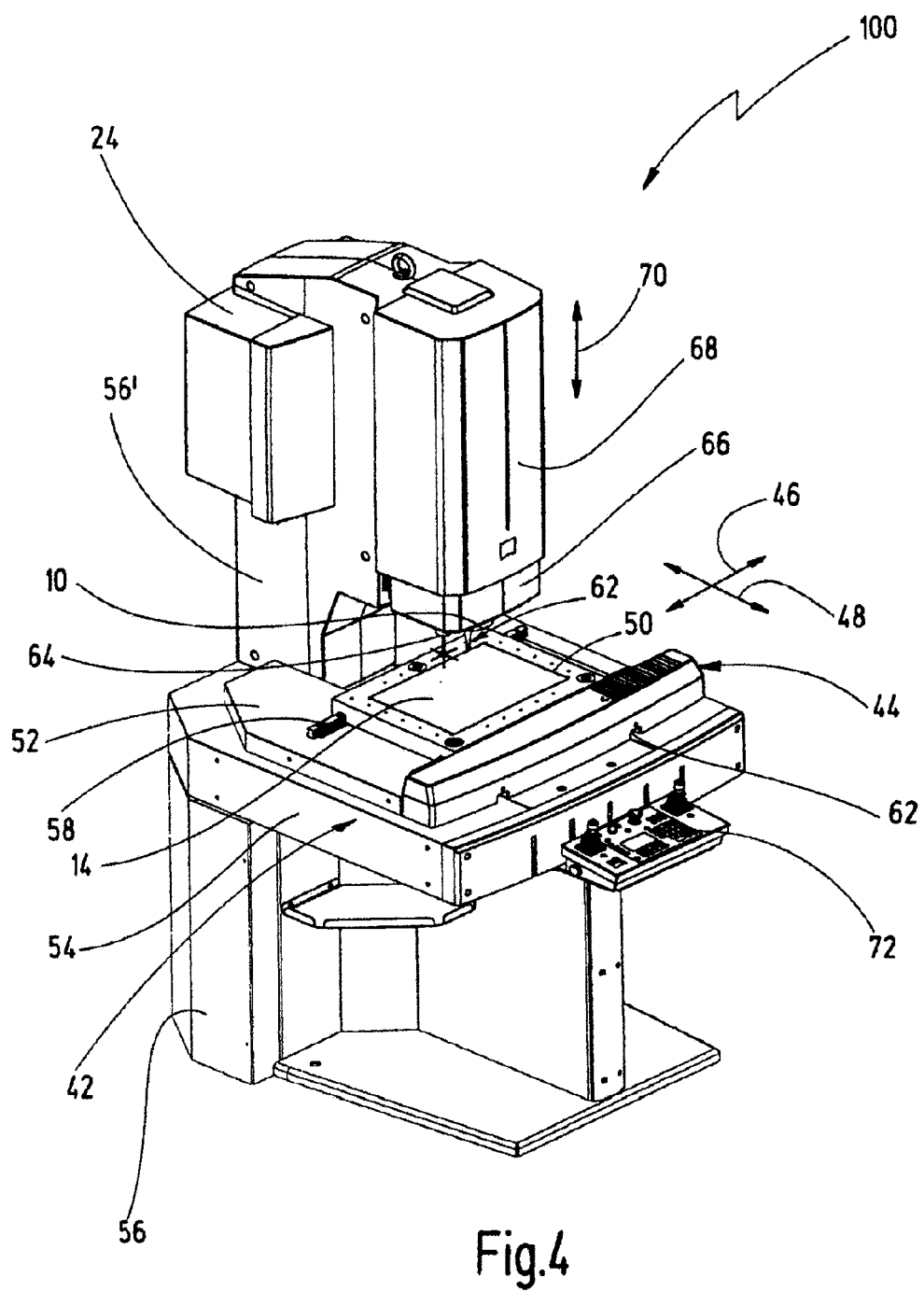
FIG. 4 shows an isometric view of a coordinate measuring machine with a further embodiment of an apparatus for inspecting an object.

FIG. 4 shows a coordinate measuring machine 100 comprising an apparatus 10.

Coordinate measuring machines are generally known in the prior art. They are used, for example in the context of quality assurance, to check workpieces or to determine the geometry of a workpiece completely in the context of so-called "reverse engineering". Furthermore, a wide variety of further application possibilities are conceivable, thus for example including the additional use for inspecting surfaces.

In such coordinate measuring machines, different types of sensors can be used to detect the coordinates of a workpiece to be measured. By way of example, sensors that effect tactile measurement are known for this purpose, such as are sold for instance by the applicant under the product designation "VAST", "VAST XT" or "VAST XXT". In this case, the surface of the workpiece to be measured is probed with a probe pin whose coordinates in the measurement space are continuously known. Such a probe pin can also be moved along the surface of a workpiece, such that in such a measuring process in the context of a so-called "scanning method" a multiplicity of measurement points can be detected at defined time intervals.

Furthermore, it is known to use optical sensors which enable the coordinates of a workpiece to be detected contactlessly. One example of such an optical sensor is the optical sensor sold by the applicant under the product designation "ViS-can".

The sensors can then be used in various types of measurement set-ups. One example of such a measurement set-up is a multisensor system of table design, as shown in FIG. 4. One example of such a multisensor system of table design is the product "O-INSPECT" from the applicant. In such a machine, both an optical sensor and a tactile sensor are used to carry out different inspection tasks on one machine and ideally with a single clamping of a workpiece to be measured. In this way, many inspection tasks for example in medical technology, plastics technology, electronics and precision mechanics can be carried out in a simple manner. It goes without saying that, furthermore, various other set-ups are also conceivable. The proposed apparatus 10 can be provided for example as a module of such a coordinate measuring machine 100. Thus, a fringe pattern method and a deflectometry method can be carried out alongside the normal tactile and/or optical measurement tasks of the coordinate measuring machine 100.

Such sensor systems or sensor heads that carry both tactile and optical sensors are becoming increasingly important in coordinate measuring technology. A combination of tactile and optical sensors makes it possible to combine in a single coordinate measuring machine the advantages of the high accuracy of a tactile measuring system with the speed of an optical measuring system. Furthermore, calibration processes during sensor changes are avoided, as is possible reclamping of a workpiece.

Traditionally, the sensor head, which can also be designated as sensor system, is connected to a carrier system that supports and moves the sensor system. Various carrier systems are known in the prior art, for example gantry systems, stand, horizontal arm and arm systems, all kinds of robot systems and finally closed CT systems in the case of sensor systems operating with X-rays. In this case, the carrier systems can furthermore have system components that enable the sensor head to be positioned as flexibly as possible. One example thereof is the rotary-pivoting articulated joint from the applicant sold under the designation "RDS". Furthermore, various adapters can be provided in order to connect the different system components of the carrier system among one another and to the sensor system.

Consequently, the use of the apparatus 10 and the coordinate measuring machine 100 are not restricted to the table set-up illustrated in FIG. 4 and the corresponding carrier system, but rather can also be used with all other types of carrier systems. Furthermore, the apparatus 10 can also generally be used in multi-sensor measuring systems or in a material microscope or in production machines.

Alongside the apparatus 10, the coordinate measuring machine 100 has a measuring table 42. A positioning device 44 is situated on the measuring table 42. Said positioning device is provided, in particular, for positioning the object 12 parallel to an X-axis 46 and to a Y-axis 48. In this case, the X-axis 46 and the Y-axis 48 span a measuring plane.

By way of example, an X-table 50 and a Y-table 52 can be provided for positioning purposes. The X-table 50 is movable parallel to the X-axis 46 and the Y-table 52 is movable parallel to the Y-axis 48. Both are arranged on a baseplate 54. The baseplate 54 is carried by a machine frame 56 and 56'.

The movement of the X-table 50 and of the Y-table 52 is guided by linear guides in the X-direction 58 and in linear guides in the Y-direction 60. This set-up corresponds to the so-called "table set-up". As already explained above, other carrier systems are also conceivable.

The coordinate measuring machine 100 has a measuring head 62. One or a plurality of tactile sensors 64 can be arranged in the measuring head 62. Furthermore, the apparatus 10 is arranged in the measuring head 62. Furthermore, one or a plurality of further optical sensors can also be arranged in the measuring head 62.

The measuring head 62 is held in a Z-slide, which is guided in a slide housing 68 parallel to a Z-axis 70. Said Z-axis 70 is perpendicular to the X-axis 46 and to the Y-axis 48. The X-axis 46, the Y-axis 48 and the Z-axis 70 thus form a Cartesian coordinate system.

The coordinate measuring machine 100 furthermore has an operating console 72. The individual elements of the coordinate measuring machine 100 can be driven by means of the operating console 72. Furthermore, it is possible to predetermine inputs at the coordinate measuring machine 100. In principle, it can also be provided that a display device (not illustrated) is arranged in the operating console 72 or elsewhere, in order to convey measurement value outputs to a user of the coordinate measuring machine 100. All other elements of the coordinate measuring machine 100 are designated by reference signs identical to those in FIGS. 1 to 3 and will not be explained again below.

Figure 5:
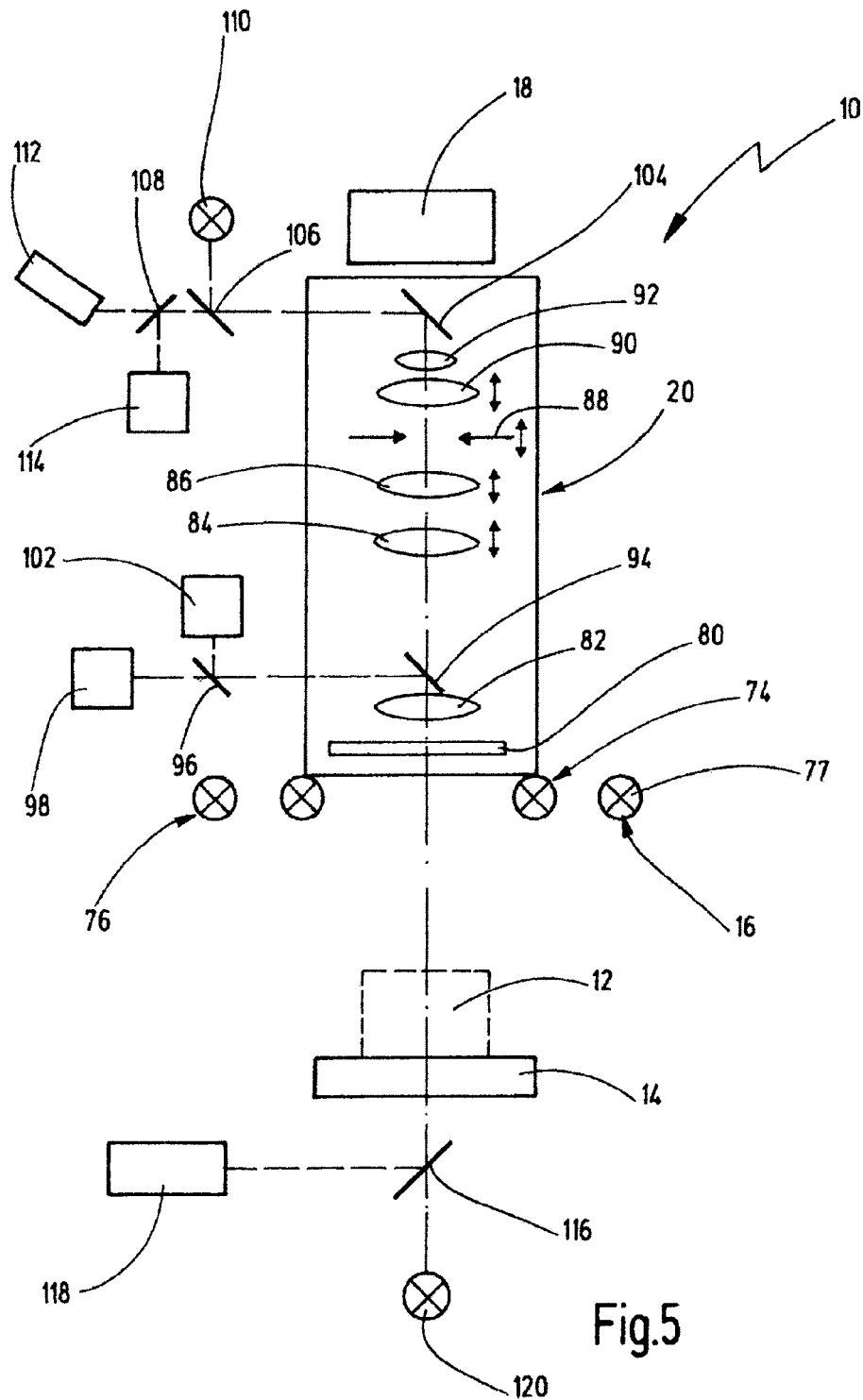
FIG. 5 shows a schematic illustration of the further embodiment of an apparatus in accordance with the present invention.

FIG. 5 schematically shows a construction of the apparatus 10 such as can be used for example in the coordinate measuring machine 100 in FIG. 4. In this case, identical elements are identified by identical reference signs and will not be explained again.

In particular, the defined construction of the imaging optics 20 can be gathered from FIG. 5. Furthermore, it is evident that the apparatus 10 can have different illumination units. Thus, by way of example, an inner ring light 74 and an outer ring light 76 can be provided. The ring lights 74, 76 can serve to illuminate the object 12 at different angles of incidence. In principle, alongside the ring lights 74, 76, other illumination units or types can also be provided. By way of example, provision can be made for a light source of the outer ring light 76 to form the light source of the pattern generating unit 16 and, consequently, for the pattern generating unit 16 to be provided in the outer ring light 76.

The imaging optics 20 has a front cover 80 in order to protect the imaging optics 20 from contamination and influences from outside. Situated behind that—as seen from the object 12—is a front lens element 82. The latter is arranged in a fixed manner, that is to say is not movable along an optical axis of the imaging optics 20.

Furthermore, the imaging optics 20 has a first lens-element group 84 a second lens-element group 86, an aperture diaphragm 88, a third lens-element group 90 and a fourth lens-element group 92. The lens-element group can have one or a plurality of lens elements which can in turn be spaced apart from one another or cemented to one another. The first lens-element group 84, the second lens-element group 86, the aperture diaphragm 88 and also the third lens-element group 90 are movable along the optical axis of the imaging optics 20. In this way, by means of a single optical design, it is possible to design an imaging optics 20 which provides the desired different operating distances and furthermore affords a zoom possibility. In particular, the imaging optics 20 can be embodied as telecentric on the object side or on both sides.

Furthermore, a first beam splitter 94 can be provided. A beam of light rays branched off by means of the first beam splitter 94 can then be split once again, if appropriate, by means of a second beam splitter 96. In this way, it may be possible, for example, for a confocal white light sensor 98 or, if appropriate, yet another sensor 102 having desired measurement properties to be coupled concentrically into the imaging optics 20.

Furthermore, a third beam splitter 104 can be arranged directly up-stream of the image capture unit 18. Further beam splittings can be effected in the branched-off beam of rays by means of a fourth beam splitter 106 and a fifth beam splitter 108. By way of example, a light source for reflected light 110, a focus camera 112 and a laser grating grid projector 114 can be arranged at these locations. The focus camera 112 and the laser grating grid projector 114 can be used for example for an autofocus unit.

A further beam splitter 116 can be provided below the object carrier 14, which is of transparent design, if appropriate. An alternative or additional confocal white light sensor 118 can be provided in this way. Furthermore, a light source for transmitted light 120 can be provided.

Figure 6:
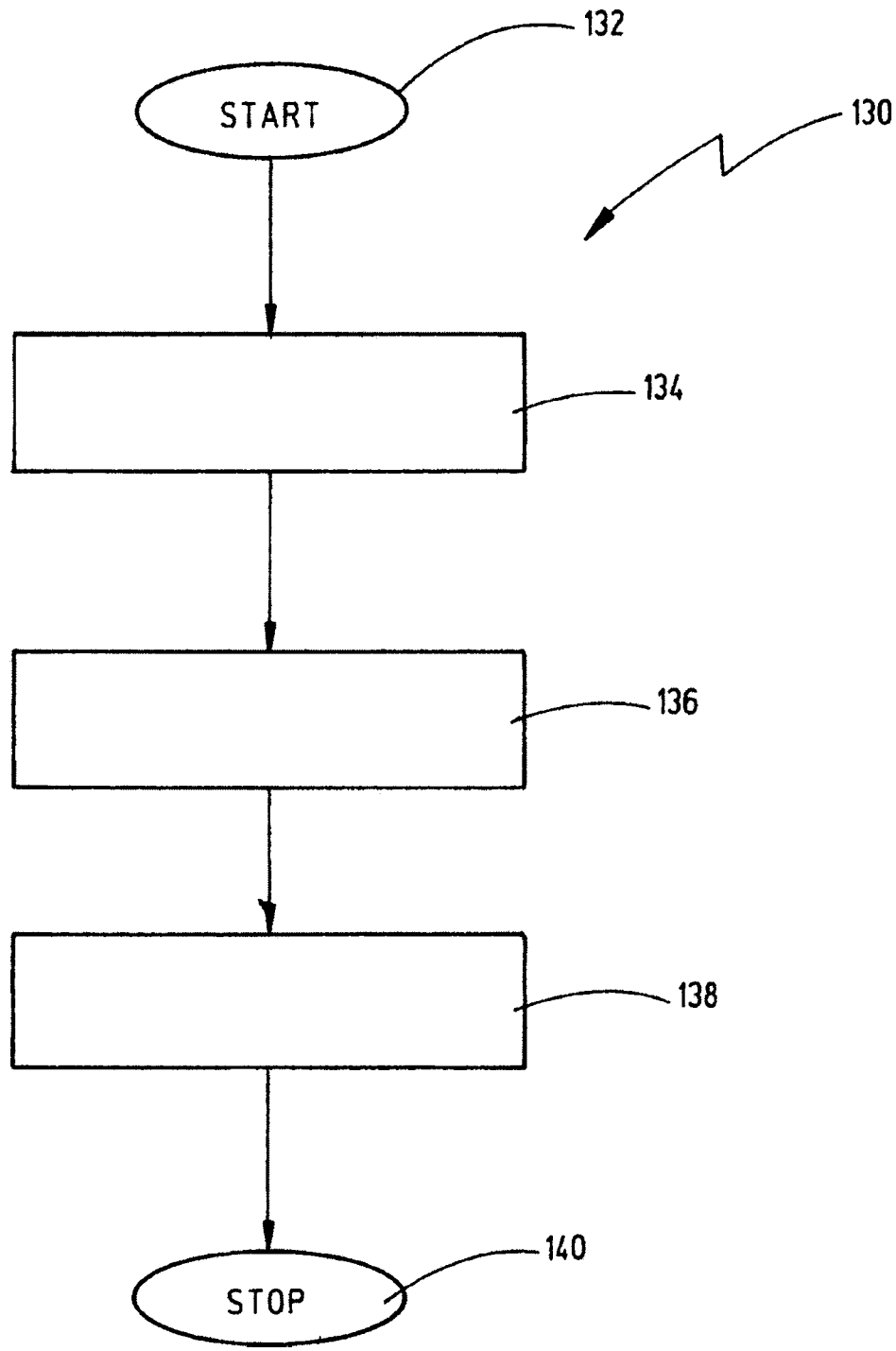
FIG. 6 shows a schematic flow chart of an embodiment of a method in accordance with the present invention.

FIG. 6 shows a schematic flow chart of a method 130.

The method 130 is provided for changing an operating mode of an apparatus 10 for inspecting an object 12. For this purpose, the apparatus 10 can be configured in accordance with the apparatus 10 illustrated in FIGS. 1 to 3 or FIGS. 4 and 5.

The method begins then in a start step 132. A step 134 firstly involves assigning a first operating distance 26 and an inactive state of the diffusing unit 30 to a first operating mode. Said first operating mode is the stripe projection method, in particular. A further step 136 involves assigning a second operating distance, which is greater than the first operating distance, and the active state of the diffusing unit 30 to a second operating mode, in particular a deflectometry method.

During the operation of the apparatus 10 or the coordinate measuring machine 100, a step 138 can then involve changing between the first operating mode and the second operating mode in any desired manner. This is done by changing between the first operating distance 26 and the second operating distance 28. This can be effected by mechanical movement of the imaging optics 20 and of the object carrier 14 relative to one another and/or by the object-side focal length of the imaging optics 20 being changed. In other words by variation of the optical operating distance and/or of the mechanical operating distance. When the operating distance is changed, at the same time the diffusing unit 30 is changed between the active state and the inactive state. A change of operating modes becomes possible in this way. In particular, it thus becomes possible to switch to and fro in any desired manner between measurement by means of a deflectometry method and a stripe projection method.

If the apparatus 10 or the coordinate measuring machine 100 is switched off, the method 130 ends in a stop step 140.

What is claimed is:

1. An apparatus for optically inspecting an object, comprising an object carrier for carrying the object, a pattern generating unit for illuminating the object with a measurement pattern, an image capture unit for capturing a number of images of the object, an imaging optics for influencing a light beam path between the object and the image capture unit, and a data processing unit, which is designed to determine at least one property of the object on the basis of the number of images, wherein the apparatus is settable to at least two operating distances which are at least a first operating distance and a second operating distance, and the apparatus has a diffusing unit, which is changeable between an active state, in which the diffusing unit influences the light beam path in front of the pattern generating unit and an inactive state, in which the diffusing unit does not influence the light beam path.

2. The apparatus as claimed in claim 1, wherein the diffusing unit, for the purpose of changing between the active state and the inactive state, is optionally movable into a light beam path in front of the pattern generating unit by the data processing unit by means of an actuator.

3. The apparatus as claimed in claim 2, wherein the diffusing unit is an etched substrate or a diffractive optical element or a holographic optical element.

4. The apparatus as claimed in claim 1, wherein the diffusing unit is an electrically drivable diffusing unit which is switchable between at least one diffusing setting and one non-diffusing setting by the data processing unit.

5. The apparatus as claimed in claim 1, wherein the pattern generating unit has a pattern generator for generating a measurement pattern and an imaging device for imaging the measurement pattern onto the object.

6. The apparatus as claimed in claim 1, wherein the apparatus can be set to at least a first optical operating distance and a second optical operating distance.

7. The apparatus as claimed in claim 1, wherein the apparatus can be set to at least a first mechanical operating distance and a second mechanical operating distance.

8. The apparatus as claimed in claim 6, wherein the imaging optics is an objective that is telecentric at the first optical operating distance on the object side or on both sides.

9. The apparatus as claimed in claim 8, wherein the imaging optics is furthermore a zoom objective.

10. The apparatus as claimed in claim 6, wherein the imaging optics can be set to a first optical operating distance, a second optical operating distance and a third optical operating distance.

11. The apparatus as claimed in claim 1, wherein the data processing unit is designed to control the state of the diffusing unit and operating distance of the imaging optics.

12. The apparatus as claimed in claim 1, wherein the apparatus is designed in such a way that, in a first operating mode, the first operating distance is set and the inactive state is chosen, and that, in a second operating mode, the second operating distance and the active state are chosen.

13. The apparatus as claimed in claim 1, wherein the second optical operating distance is two to two-and-a-half times the magnitude of the first optical operating distance.

14. The apparatus as claimed in claim 1, wherein the first optical operating distance is 80 mm and the second optical operating distance is 200 mm, or wherein the first optical operating distance is 40 mm and the second optical operating distance is 80 mm.

15. The apparatus as claimed in claim 1, wherein the data processing unit is designed to carry out as first operating mode a fringe pattern method and as second operating mode a deflectometry method for optically inspecting the object.

16. The apparatus as claimed in claim 6, wherein the apparatus can be set to at least a first mechanical operating distance and a second mechanical operating distance.

17. A method for changing an operating mode of an apparatus for optically inspecting an object, wherein the apparatus comprises an object carrier for carrying the object, a pattern generating unit for illuminating the object with a measurement pattern, an image capture unit for capturing a number of images of the object, an imaging optics for influencing a light beam path between the object and the image capture unit, wherein the apparatus is settable to at least two operating distances which are at least a first operating distance and a second operating distance, a data processing unit, which is designed to determine at least one property of the object on the basis of the number of images and to control the apparatus, and a diffusing unit, which is changeable between an active state, in which the diffusing unit influences a light beam path in front of the pattern generating unit and an inactive state, in which the diffusing unit does not influence the light beam path, in front of the pattern generating unit, comprising the following steps:
   assigning the first operating distance and the inactive state to a first operating mode,
   assigning the second operating distance, which is greater than the first operating distance, and the active state to a second operating mode,
   changing between the first operating mode and the second operating mode by changing the operating distance of the imaging optics between the first operating distance and the second operating distance and changing the diffusing unit from the active state to the inactive state.

18. The method as claimed in claim 17, wherein the first operating mode is a fringe pattern method and the second operating mode is a deflectometry method.

* * * * *